United States Patent [19]

Raghu et al.

[11] 4,314,066
[45] Feb. 2, 1982

[54] SYNTHESIS OF TETRAMISOLE, LEVAMISOLE AND THEIR DERIVATIVES

[75] Inventors: Sivaraman Raghu, Norwalk; Arthur K. Hoffmann, New Canaan; Balwant Singh, Stamford, all of Conn.

[73] Assignee: American Cyanamid Co., Stamford, Conn.

[21] Appl. No.: 878,049

[22] Filed: Feb. 15, 1978

Related U.S. Application Data

[60] Division of Ser. No. 739,923, Nov. 8, 1976, Pat. No. 4,087,611, which is a continuation-in-part of Ser. No. 680,302, Apr. 26, 1976, abandoned.

[51] Int. Cl.$^3$ ........................................... C07D 233/38
[52] U.S. Cl. ..................................................... 548/320
[58] Field of Search ......................................... 548/320

[56] References Cited

U.S. PATENT DOCUMENTS 2,441,935  5/1948  Duschinsky ........................ 548/321
3,849,480  11/1974 Knowles ............................ 560/250
4,119,652  10/1978 Knowles ......................... 260/429 R

OTHER PUBLICATIONS

Hofmann, Imidazole and Its Derivatives, Part 1, Interscience Publishers, New York (1953), pp. 235–236.

Primary Examiner—Richard Raymond
Attorney, Agent, or Firm—H. G. Jackson

[57] ABSTRACT

A process for the manufacture of 1-(2-alkoxyethyl)-4-phenyl-4-imidazolin-2-ones, 1-(2-alkoxyethyl)-4-phenyl-2-imidazolidones, 1-(2-alkoxyethyl)-4-phenylimidazolidine-2-thiones, certain of the corresponding 1-(2-hydroxyethyl) derivatives, and their 3-acylated derivatives, and certain related compounds which are all useful as intermediates in a new process for the manufacture of the anthelmintic levamisole, (−)-2,3,5,6-tetrahydro-6-phenylimidazo-[2,1-b]thiazole, and its derivatives through conventional resolution procedures. The new process also permits the direct manufacture of optically active 1-(2-alkoxyethyl)-4-phenyl-2-imidazolidone and their 3-acylated derivatives, optically active 1-(2-alkoxyethyl)-4-phenylimidazolidine-2-thiones, and levamisole, the levorotatory isomer of tetramisole, using catalytic amounts of a chiral reducing agent, with the elimination of conventional resolution procedures.

5 Claims, No Drawings

SYNTHESIS OF TETRAMISOLE, LEVAMISOLE AND THEIR DERIVATIVES

This is a division of application Ser. No. 739,923, filed Nov. 8, 1976, now U.S. Pat. No. 4,087,611, which application is a continuation-in-part of our copending application, Ser. No. 680,302, filed Apr. 26, 1976, now abandoned.

BACKGROUND OF THE INVENTION

There are several procedures for the production of the anthelmintic tetramisole reported in the literature (Raeymaekers et al., J. Med. Chem. 9, 545 (1966), Bakelien et al., Aust. J. Chem. 21 1557 (1968), T. R. Roy U.S. Pat. No. 3,855,234, M. E. McMenin, U.S. Pat. No. 3,845,070). These procedures yield tetramisole, a racemic compound, which is then resolved to give its physiologically active levorotatory enantiomer levamisole. None of these procedures is adaptable to a direct synthesis of levamisole without resolution.

A method for making tetramisole from 1-(2-hydroxyethyl)-4-phenyl-4-imidazolin-2-thione and thionyl chloride is disclosed in U.S. Pat. No. 3,726,894. This compound is made by the hydroboration reaction on 1-vinyl-4-phenyl-4-imidazolin-2-thione, which is obtained as a by-product in the racemization of physiologically inactive d-tetramisole to the physiologically active dl-compound, tetramisole.

The literature reports two methods for the synthesis of levamisole without its resolution (Raeymaekers et al., Tetrahedron Letters, 1467 (1967) and P. R. Dick. French Pat. No. 2224-472).

The stereoselective synthesis of levamisole by the Raeymaekers method involves the condensation of optically active α-phenylethylenediamine which carbon disulfide, followed by the reaction of the resulting 4-phenyl-imidazolidine-2-thione with ethylene bromide. The synthesis requires optically active α-phenylethylenediamine, which has to be prepared by resolution. Thus resolution is not avoided, only placed back in the reaction sequence. The ring closure with ethylene bromide on the intermediate described would also produce some "isolevamisole" (2,3,4,5-tetrahydro-5-phenylimidazo(2,1-b)thiazole) which would have to be separated. No mention of this separation has been made in the above publication.

The second stereospecific synthesis of levamisole is disclosed in the above-mentioned French Patent. This involves the reaction of 2-substituted thiazolidines with optically active 2-phenylaziridine and subsequent ring closure. This synthesis also requires the preparation of the optically active intermediate 2-phenyl aziridine through a resolution procedure, and the condensation will also produce some undesired "isolevamisole", which must be separated. Additionally, the possible carcinogenicity of the 2-phenylaziridine (low molecular weight aziridines have proven carcinogenic) makes the process hazardous to run and requires extraordinary care to assure absence of the intermediate in the final product.

The instant invention overcomes all these drawbacks in that it is regioselective (no isolevamisole can be formed); all the steps occur in good yields; it involves for the first time in levamisole synthesis a catalytic reduction step, amenable to introducing chirality using catalytic amounts of a chiral reagent. The synthesis is even expected to be more economical than the current routes for tetramisole; and it is applicable to the synthesis of other analogs.

FIELD OF THE INVENTION

The instant invention relates to the synthesis of 1,4-disubstituted 4-imidazoline-2-ones, 1,4-disubstituted imidazolidine-2-ones, 1,4-disubstituted imidazolidine-2-thiones, and their subsequent conversion to levamisole and substituted levamisoles.

SUMMARY OF THE INVENTION

The instant invention relates to a novel process, using novel intermediates, for the production of levamisole. It involves simpler and fewer steps, and avoids the use of expensive reducing agents. For the first time a catalytic assymmetric synthesis of levamisole has been achieved through the reduction of a prochiral intermediate. All other known processes proceed through the expensive resolution of tetramisole or intermediates. The instant invention is capable of producing the appropriate acid-addition salts of tetramisole or levamisole directly. The instant invention is applicable to the production of analogs of tetramisole and levamisole.

The instant invention is based on the synthesis of the catalytically reducible, appropriately substituted imidazolinone (IV) or derivative. This is achieved by reaction of the α-substituted ketone (I) with an amine such as (II) to give the intermediate α-(2-substituted ethyl)aminoketone (III).

$$R_2-\overset{O}{\underset{\|}{C}}-CH_2-X + H_2N-CH_2-CH_2-OR \xrightarrow[\substack{0°-50° C. \\ OH^-}]{\text{Solvent}}$$

(I) \qquad\qquad (II)

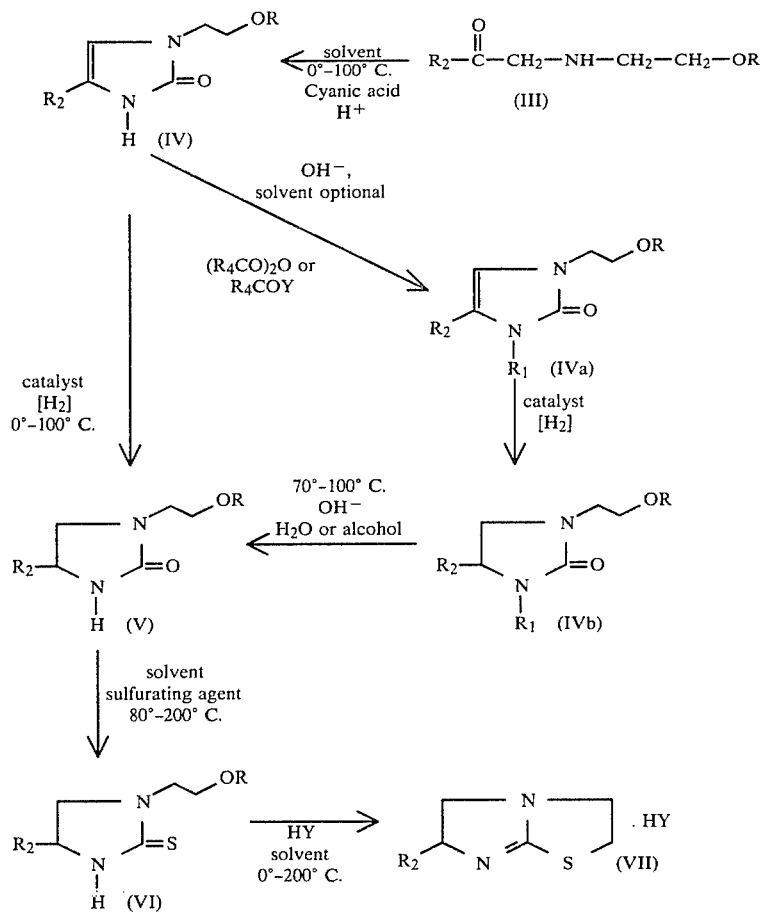

(R, $R_1$, $R_2$, $R_4$, X and Y are defined in the following paragraphs)

An α-substituted ketone of formula I, wherein $R_2$ is selected from the group consisting of phenyl, and substituted with up to two groups selected from the group consisting of lower alkyl, lower alkoxy, halo, and trifluoromethyl and X is a group (such as chlorine, fluorine, bromine, iodine and p-toluene sulfonate) which can be displaced by a nucleophilic reagent, is reacted with an amine of formula II, or its acid addition salts, wherein R is selected from the group consisting of hydrogen, $C_1$-$C_6$ alkyl, halo $C_1$-$C_6$ alkyl and phenyl, optionally substituted with up to five groups selected from the group consisting of lower alkyl, halo and lower alkoxy, and a moiety of the formula $COR_3$, wherein $R_3$ is selected from the group consisting of hydrogen, $C_1$-$C_6$ alkyl, $C_1$-$C_6$ alkoxy, phenoxy, halo $C_1$-$C_6$ alkyl, phenyl, and phenyl or phenoxy substituted with up to four groups selected from the group containing of lower alkyl, halo, lower alkoxy, and trifluoromethyl to yield the compound of formula III. This reaction can be run using an excess of the compound of formula II, or in the presence of a tertiary amine such as triethylamine, or in the presence of a hydroxide source such as sodium carbonate, at a temperature from about 0° to about 50° C. in a solvent (such as alcohol or halocarbon) from about 30 minutes to about 3 hours.

Compound III is dissolved in any suitable organic solvent (such as methanol, chloroform or methylene chloride), heated from about 0° to about 100° C. in the presence of cyanic acid and a suitable hydronium source to yield the imidazolinone of the formula IV.

Two alternative routes for the production of the imidazolidone of formula V are feasible. In the first of these two routes the imidazolinone of formula IV (where $R_2$ is a phenyl and a phenyl substituted with up to two groups selected from the group consisting of lower alkyl, lower alkoxy, halo, and trifluoromethyl is hydrogenated at about 15 to about 1000 psig of hydrogen in a suitable solvent (such as alcohol, hydrocarbon, mixed alcohol-hydrocarbon solvent or acetic acid) in the presence of a catalyst (such as palladium on carbon) at a temperature from about 0° to about 100° C. for about 30 minutes or more, or reduced with a suitable reducing agent, to yield the imidazolidone of formula V. Alternatively, IV is reacted with an acyl halide or acyl anhydride of the formula:

$R_4COY$ or $(R_4CO)_2O$ wherein $R_4$ is selected from the group consisting of $C_1$-$C_6$ alkyl, $C_5$-$C_{10}$ cycloalkyl, phenyl, and phenyl or phenoxy substituted with up to four groups selected from the group consisting of lower alkyl, lower alkoxyl, halo and trifluoromethyl, and Y is any group (such as halogen) which can be displaced by a nucleophilic reagent, in the presence of a hydroxide source while refluxing neat or in a hydrocarbon solvent to yield the imidazolinone of formula IVa. The imidazolinone of formula IVa (wherein $R_1$ and $R_2$ are as defined above and $R_1$ is $R_4CO$ wherein $R_4$ is as defined above is hydrogenated under the same conditions for IV V to yield the imidazolidone of formula IVb. In the course of the hydrogenation of either IV or IVa, any halogens that may be present as part of the R, $R_1$, or $R_3$ groups will be removed and replaced by hydrogen unless mild conditions of hydrogenation or other reduction are used. The imidazolidone of formula IVb is hydrolyzed in the presence of a hydroxide source in either water or alcohol at a temperature from about 70° to 100° C. to yield the imidazolidone of formula V. It is generally found in the case of IVb with R equal to $COR_3$ that the $COR_3$ group is also hydrolyzed in this step to give V with R equal to hydrogen.

The imidazolidone of formula V (wherein $R_2$ is as defined for Compound IV above) is heated in an inert solvent (such as toluene, xylene or cyclohexane) at a temperature from about 80° to about 200° C. in the presence of a reagent (such as phosphorus pentasulfide) capable of substituting sulfur for oxygen to yield the imidazolidinethione of formula VI and some of the compound of formula VII (as a free base). In the case of formula V compounds wherein R is hydrogen, reaction with phosphorus pentesulfide also affects the free hydroxyl group, altering it to form a sulfur-containing group which may or may not also contain phosphorus. This altered group is nontheless capable of undergoing ring closure in the final step to firm compounds of formula VII. In the case of formula V compounds wherein R is the $COR_3$ moiety, it is frequently found that the $COR_3$ group reacts with the thiating reagent (e.g., phosphorus, pentasulfide) to form the $CSR_3$ group. This does not affect the ability of the formula VI compounds in which this change has occured to ring close to the useful compounds of formula VII.

The imidazolidinethione of formula VI (wherein $R_2$ is as defined for Compound IV above) is heated with HY, wherein Y is a pharmaceutically acceptable anion (such as chloride, fluoride, iodide, bisulfate, p-toluenesulfonate) in a solvent at a temperature from about 0° to about 200° C. to yield the compound of formula VII. The compound of formula III wherein R is an acyl group may also be made as follows:

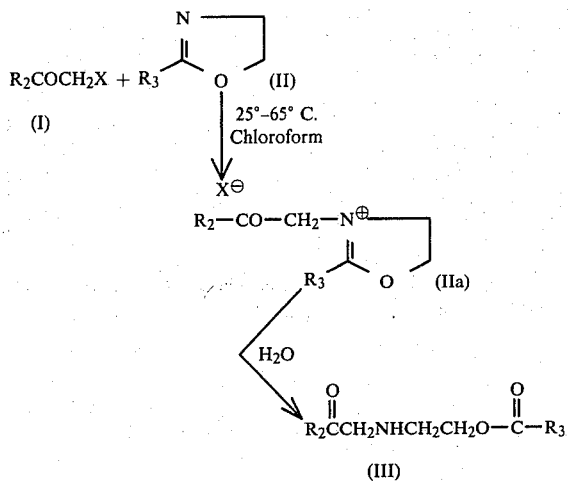

The compound of formula IVa undergoes homogeneous reduction, as shown in the following flowsheet, with a chiral catalyst, such as compound VIII, when hydrogenated at from about 15 to about 1500 psig of hydrogen in a suitable organic solvent such as alcohol or aromatic solvents at a temperature from about 25° to about 80° C. Compound Va is hydrolyzed, when heated from about 70° to about 100° C. in the presence of a hydroxide source in water or alcohol, to optically active compound Vb. Racemic mixture V, from the first flowsheet, or optically active Vb, from the following flowsheet is converted to racemic VI or optically active VIb, respectively, along with some racemic VII and optically active VIIb, respectively, on treatment with a reagent capable of substituting sulfur for oxygen in refluxing hydrocarbon solvents at a temperature from 80° to about 200° C. As indicated above, other oxygen functions that may be present in V or Vb may also undergo reaction with the thiating reagent. The compounds of formula VI and VIb are converted to racemic VII and optically active VIIb, respectively, on heating with HY, wherein Y is a pharmaceuticaly acceptable anion (such as chloride, fluoride, iodide, bisulfate, p-toluene sulfonate, and the like) in a suitable solvent at a temperature from about 0° to about 200° C.

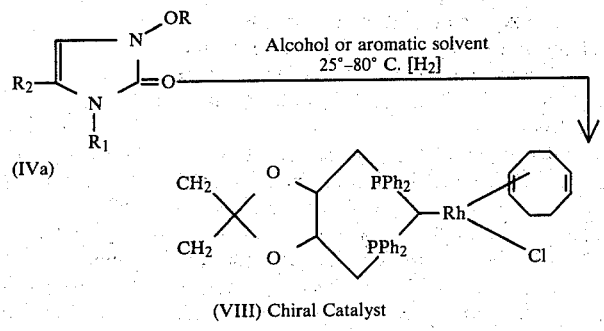

(VIII) Chiral Catalyst

-continued

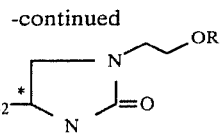
(Va)

70°-100° C.
water or
alcohol
OH⁻

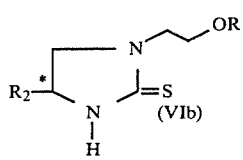          sulfurating agent solvent          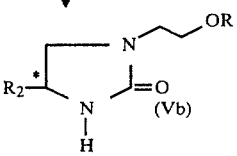
(VIb)              80°-200° C.                                   (Vb)

and (VIIb) as the optically active free base

HY
solvent
0°-200° C.

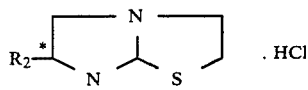 . HCl (VIIb)

Some of the novel optically active compounds of this invention can be described by the formula:

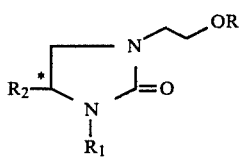

wherein R is selected from the group consisting of hydrogen, $C_1-C_6$ alkyl, halo $C_1-C_6$ alkyl, phenyl, phenyl substituted with up to three groups selected from the group consisting of $C_1-C_6$ alkyl, halo and $C_1-C_6$ alkoxy and a moiety of the formula $COR_3$, wherein $R_3$ is selected from the group consisting of hydrogen, $C_1-C_6$ alkyl, $C_1-C_6$ alkoxy, phenoxy, halo $C_1-C_6$ alkyl, phenyl, and phenyl substituted with up to four groups selected from the group consisting of $C_1-C_6$ alkyl, halo, trifluoromethyl and $C_1-C_6$ alkoxy; $R_1$ is selected from the group consisting of hydrogen and a moiety of the formula $COR_4$, wherein $R_4$ is selected from the group consisting of $C_1-C_6$ alkyl, $C_1-C_6$ alkoxy, phenoxy, $C_5-C_{10}$ cycloalkyl, phenyl, and phenyl or phenoxy substituted with up to four groups selected from the group consisting of $C_1-C_6$ alkyl, halo and trifluoromethyl; and $R_2$ is selected from the group consisting of phenyl and phenyl substituted with up to two groups selected from the group consisting of $C_1-C_6$ alkyl, $C_1-C_6$ alkoxy, halo and trifluoromethyl.

A preferred embodiment of the present invention are the optically active compounds of the above shown formula, wherein R is selected from the group consisting of hydrogen, $C_1-C_6$ alkyl, phenyl and a moiety of the formula $COR_3$, wherein $R_3$ is selected from the group consisting of hydrogen, $C_1-C_6$ alkyl and phenyl; $R_1$ is selected from the group consisting of hydrogen and a moiety of the formula $COR_4$, wherein $R_4$ is selected from the group consisting of $C_1-C_6$ alkyl, $C_1-C_6$ alkoxyphenyl, $C_5-C_6$ cycloalkyl, phenyl and trifluoromethylphenyl; and $R_2$ is selected from the group consisting of phenyl, and m-halophenyl.

A most preferred embodiment of the present invention are optically active compounds of the above shown formula, wherein R is selected from the group consisting of hydrogen $C_1-C_4$ alkyl, phenyl, and a moiety of the formula $COR_3$, wherein $R_3$ is selected from the group consisting of hydrogen, $C_1-C_6$ alkyl, and phenyl; $R_1$ is selected from the group consisting of hydrogen and a moiety of the formula $COR_4$, wherein $R_4$ is selected from the group consisting of $C_1-C_4$ alkyl, phenyl, $C_1-C_4$ alkoxyphenyl and trifluoromethylphenyl; and $R_2$ is phenyl.

Some of the novel optically active compounds of this invention can be described by the formula:

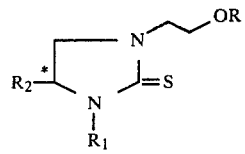

wherein R is selected from the group consisting of $C_1-C_6$ alkyl, halo $C_1-C_6$ alkyl, phenyl, phenyl substituted with up to three groups selected from the group consisting of $C_1-C_6$ alkyl, halo and $C_1-C_6$ alkoxy; and $R_2$ is selected from the group consisting of phenyl and phenyl substituted with up to two groups selected from the group consisting of $C_1-C_6$ alkyl, $C_1-C_6$ alkoxy, halo and trifluoromethyl.

A preferred embodiment of the present invention are the optically active compounds of the above shown formula, wherein R is selected from the group consisting of $C_1$–$C_6$ alkyl and phenyl; and $R_2$ is selected from the group consisting of phenyl, and m-halophenyl.

EXAMPLE 1

1-(2-Methoxyethyl)-4-phenyl-4-imidazolin-2-one

Phenacyl bromide (60 g.), in 200 ml. of methylene chloride, is added over one hour to 2-methoxyethylamine (52 g.), in 100 ml. of methylene chloride, and cooled with an ice bath. The mixture is stirred for two hours at 0° C. Water (400 ml.) is added and the organic layer is separated, dried over anhydrous sodium sulfate and concentrated under aspirator vacuum (at room temperature). The viscous oil (260 g.) is dissolved in methanol (200 ml.), cooled to 0° C. and acetic acid (80 ml.) and potassium cyanate (30 g.) is added. The mixture is refluxed for 90 minutes, the solvent removed under reduced pressure and the residue is taken up in 600 ml. of chloroform and washed with saturated sodium bicarbonate solution. The chloroform layer is washed, dried over sodium sulfate and concentrated to give a semisolid. Trituration with ether and filtration yields the title product as a yellow crystal; m.p. 152°–153° C.

EXAMPLE 2

1-(2-methoxyethyl)-4-phenyl-4-imidazolin-2-one

Phenacyl bromide (199 g.), in 400 ml. of chloroform, in added over one half hour to a mixture of 2-methoxyethylamine (82 g) and triethylamine (152 g.) in 200 ml. of chloroform at 0° C. The mixture is stirred for two hours at 0°–10° C. Water (400 ml.) is added and the organic layer is separated and washed with another 400 ml. of water. The chloroform layer is cooled to 0° C. with an ice bath and glacial acetic acid (72 g.) potassium cyanate (89 g.) and methanol (100 ml.) are added. The mixture is refluxed for ninety minutes, cooled and washed with saturated sodium bicarbonate solution, and the organic layer is dried over anhydrous sodium sulfate and then concentrated to give a semisolid. Trituration with 300 ml of ether and filtration gives the title product as a yellow crystal; m.p. 152°–154° C.

EXAMPLE 3

1-(2-methoxyethyl)-4-phenyl-2-imidazolidone

Approximately 10.9 g. of 1-(2-methoxyethyl)-4-phenyl-4-imidazolin-2-one and 1 g. of 10% palladium on carbon in 100 ml of ethanol is hydrogenated in a Parr Shaker apparatus at 30 psig of hydrogen for 45 minutes. The crystal is filtered, washed with ethanol, and the filtrate is concentrated to give the title compound as a waxy white solid; m.p. 82°–83° C.

The above reduction can also be carried out with acetic acid as the solvent, and at atmospheric pressure in either solvent.

EXAMPLE 4

1-(2-methoxyethyl)-4-phenylimidazolidine-2-thione

Approximately 1 g. of 1-(2-methoxyethyl)-4-phenyl-2-imidazolidone and 0.4 g. of phosphorous pentasulfide are refluxed in toluene overnight (16 hours). The toluene is distilled off under reduced pressure and the residual semisolid is dissolved in a solution of 50 ml. of chloroform and 30 ml. of 20% sodium hydroxide. The organic layer is separated, washed, dried and the solvent removed to give 1 g. of an oil. The oil is dissolved in 3 ml. of acetone and anhydrous hydrogen chloride is bubbled in for two minutes. The precipitated tetramisole hydrochloride is filtered off and the filtrate concentrated to dryness. The filtrate is recrystallized from benzene-cyclohexane to yield the title compound as a white solid; m.p. 76°–78° C.

EXAMPLE 5

Preparation of tetramisole hydrochloride from 1-(2-methoxyethyl)-4-phenylimidazolidine-2-thione Approximately 236 mg. of 1-(2-methoxyethyl)-4-phenylimidazolidine-2-thione, 5 ml. of concentrated hydrochloric acid, and 5 ml. of acetone are refluxed together for one hour. The solution is then concentrated to dryness under reduced pressure and triturated with 2 ml. of ethanol. The white solid precipitate is filtered off to yield the title compound.

EXAMPLE 6

Preparation of tetramisole hydrochloride from 1-(2-methoxyethyl)-4-phenyl-2-imidazolidone Approximately 4.4 g. of 1-(2-methoxyethyl)-4-phenyl-2-imidazolidone and 2 g. of phosphorous pentasulfide are refluxed together in 200 ml. of toluene for 20 hours. The toluene is distilled off under reduced pressure and the residue is taken in 100 ml. of chloroform and washed with 50 ml. of 20 percent sodium hydroxide solution. The organic layer is washed with water, dried and the solvent removed to give a yellow oil. The oil is refluxed for one hour in a solution of 10 ml. of concentrated hydrochloric acid and 10 ml. of ethanol. The solution is concentrated to dryness, the residual semisolid triturated with ethanol (20 ml.), filtered and dried to yield the title compound; m.p. 260°–262° C.

EXAMPLE 7

1-(2-hydroxyethyl)-4-phenyl-4-imidazolin-2-one

Phenacyl bromide (60 g.), in methylene chloride (100 ml.), is added over a period of 30 minutes to monoethanol amine (41 g.) in methylene chloride (100 ml.). The solution is cooled to 0° C. with an ice bath, stirred for another 90 minutes at 0°–5° C., and then 400 ml. of water is added. The organic layer is separated, dried over anhydrous sodium sulfate, and concentrated under reduced pressure at approximately room temperature. The residual oil is dissolved in methanol (150 ml.), cooled, and a solution of sodium cyanate (24 g.) in acetic acid (30 ml.) is added. The mixture is refluxed for one hour and then cooled. The white solid precipitate is filtered, washed with water, methanol and then dried to yield the title product; m.p. 203°–205° C.

EXAMPLE 8

1-(2-hydroxyethyl)-4-phenyl-2-imidazolidone

A slurry of 1-(2-hydroxyethyl)-4-phenyl-4-imidazolin-2-one (10.2 g.) and 10 percent palladium on carbon (1 g.) in ethanol (200 ml.) is hydrogenated in a Parr Shaker apparatus at approximately 30 psig of hydrogen for three hours. The catalyst is then filtered, washed with ethanol, and the combined filtrate and washings are concentrated to give a colorless oil which solidifies on standing to yield the title compound; m.p. 60°–63° C.

EXAMPLE 9

Preparation of tetramisole hydrochloride from 1-(2-hydroxyethyl)-4-phenyl-2-imidazolidone A mixture of 1-(2-hydroxyethyl)-4-phenyl-2-imidazolidone (4.1 g.) and phosphorous pentasulfide (1.8 g) in toluene (25 ml.) is refluxed for twenty hours. The toluene is distilled off under reduced pressure and the residue is dissolved in a solution of chloroform (50 ml.) and 20 percent sodium hydroxide (50 ml). The organic layer is separated, washed, dried over sodium sulfate concentrated to an oil. The oil is refluxed in a solution of ethanol (10 ml.) and concentrated hydrochloric acid (20 ml.) for one hour. The solution is concentrated to dryness, triturated with ethanol (20 ml.), and filtered to yield the title compound as a white solid; m.p. 260° C.

EXAMPLE 10

1-(2-Acetoxyethyl)-4-phenyl-2-imidazolidone

Approximately 9.2 g of 1-(2-hydroxyethyl-4-phenyl-2-imidazolidone is stirred with acetic anhydride (25 ml.) and p-toluenesulfonic acid (200 mg.) for four hours, during which time the imidazolidone completely dissolves. The solution (100 ml.) from which a white solid precipitates. The solid is extracted with methylene chloride (3×100 ml.). The organic layer is separated, dried and the solvent removed to give a pale yellow solid. Recrystallization from either gives the title compound as a white crystalline solid; m.p. 88°–90° C.

EXAMPLE 11

Preparation of tetramisole hydrochloride from 1-(2-acetoxyethyl)-4-phenyl-2-imidazolidone Approximately 5 g. of 1-(2-acetoxyethyl)-4-phenyl-2-imidazolidone and 1.8 g. of phosphorous pentasulfide is refluxed in 20 ml. of toluene for twenty hours. The solvent is distilled off under reduced pressure and the residue is dissolved in a solution of chloroform (100 ml.) and 20 percent sodium hydroxide (100 ml.). The organic layer is then separated, washed, dried over sodium sulfate treated with charcoal, filtered and concentrated to an oil. The oil is refluxed in a solution of concentrated hydrochloric acid (20 ml.) and ethanol (10 ml.) for one hour. The solution is concentrated to dryness and the residue triturated with ethanol (20 ml.) and then filtered to yield the title compound with a tan coloration; m.p. 258°–260° C.

EXAMPLE 12

1-(2-acetoxyethyl)-4-phenyl-4-imidazolin-2-one

Approximately 9 g. of 2-methyloxazoline and 20 g. of phenacyl bromide is refluxed in 100 ml. of chloroform for one hour. The solvent is concentrated under reduced pressure and acetic acid (10 ml.), potassium cyanate (9 g.), and methanol (100 ml.) is added to the residual oil and the mixture refluxed for one hour. The methanol is removed under reduced pressure and the residue taken up in 200 ml. of methylene chloride and washed with saturated sodium bicarbonate solution. The organic layer is dried and concentrated to a semisolid. Recrystallization from benzene-cyclohexane yields the title compound; m.p. 120°–122° C.

EXAMPLE 13

Reduction of 1-(2-acetoxyethyl)-4-phenyl-4-imidazolin-2-one

Approximately 1 g. of 1-(2-acetoxyethyl)-4-phenyl-4-imidazolin-2-one and 250 mg. of 10% palladium on carbon in 10 ml. of ethanol is stirred in an atmosphere of hydrogen. After about three-quarters of an hour the catalyst is filtered and washed with 20 ml. of ethanol. The combined filtrates is concentrated to yield the title compound as a white solid; m.p. 86°–88° C.

EXAMPLE 14

1-(2-methoxyethyl)-3acetyl-4-phenyl-4-imidazolin-2-one

Approximately 21.8 g of 1-(2-methoxyethyl)-4-phenyl-4-imidazolin-2-one and 120 ml. of acetic anhyride is refluxed together for four hours. The acetic anhydride is distilled out at reduced pressure. The residual semisolid is recrystallized from ether to yield the title compound as a white solid; m.p. 73°–75° C.

EXAMPLE 15

Racemic 1-(2-methoxyethyl)-3-acetyl-4-phenyl-2-imidazolidone

Approximately 3.9 g. of 1-(2-methoxyethyl)-3-acetyl-4-phenyl-4-imidazolin-2-one and 400 mg. of 10% palladium on carbon in 30 ml. of ethanol is hydrogenated in the Parr Shaker apparatus at 30 psig of hydrogen. After one hour the catalyst is filtered and washed with 50 ml. of ethanol. The combined filtrate is concentrated to yield the total compounds as a colorless oil.

EXAMPLE 16

Hydrolysis of 1-(2-methoxyethyl)-3-acetyl-4-phenyl-2-imidazolidone to 1-(2-methoxyethyl)-4-phenyl-2-imidazolidone Approximately 2.6 g of the 3 acetyl derivative is refluxed in 20 ml. of 10 percent sodium hydroxide for one hour. The solution is cooled and then extracted with chloroform (2×20 ml.). The combined chloroform extract is washed, dried over sodium sulfate and concentrated to give the title compound as a solid; m.p. 81°–83° C.

EXAMPLE 17

1-(2-methoxyethyl)-3-benzoyl-4-phenyl-4-imidazolin-2-one

Approximately 4.36 g. of 1-(2-methoxyethyl)-4-phenyl-4-imidazolin-2-one, 3 g. of triethylamine and 3 g. of benzoyl chloride are refluxed together for three hours in chloroform. The solution is cooled, washed with water, dried and the solvent removed to give an oil which is the O-benzoyl ester. The ester is refluxed for three hours in 20 ml. of xylene. The xylene is removed at reduced pressure. Recrystallization from ether gives the title compound as a pale yellow solid; m.p. 112°–117° C.

EXAMPLE 18

1-(2-methoxyethyl)-3-benzoyl-4-phenyl-4-imidazolin-2-one

Approximately 21.8 g. of 1-(2-methoxyethyl)-4-phenyl-4-imidazolin-2-one, 14.5 g. of benzoyl chloride and 20 g. of tri-n-butylamine are refluxed together in 60 ml of xylene for sixteen hours. The solvent is distilled off under reduced pressure and the remaining viscous oil is dissolved in 300 ml. of benzene. The benzene solution is washed with water (2×100 ml.), dried over sodium sulfate, and the solvent removed to give a semisolid. Recrystallization from ether gives the title compound as Eu(tic)₃. The results of the hydrogenations are summarized in the following table.

The catalyst is prepared from (−) tartaric acid as described by H. B. Kagan and T. P. Dang. J. Am. Chem. Soc. 94, 6429 (1972). The (+) DIOP can also be bought from Strem Chemicals, Inc. Beverly, Mass.

TABLE I

| Reduction of N-Acyl Imidazolinones with (+)DIOP-RhCODCl Catalyst and Hydrogen | | | | | | |
|---|---|---|---|---|---|---|
| Substrate | Solvent | Temp. °C. | Pressure Psig | Time Hours | Selectivity S/R | Enantiomeric Excess or Optical Yields |
| 1-(2-methoxyethyl)-3-benzoyl-4-phenyl-4-imidazolin-2-one | (1:1) | 40° | 55 | 18 | 1.65:1.0 | 25% |
| 1-(2-methoxyethyl)-3-benzoyl-4-phenyl-4-imidazolin-2-one | φH—ETOH (3:1) | 60° | 1000 | 6 | 1.25:1.0 | 11.1% |
| 1-(2-methoxyethyl)-3-cyclohexanecarbonyl-4-phenyl-4-imidazolin-2-one | φH—ETOH (1:1) | 25° | 45 | 20 | 2.0:1.0 | 33% |
| 1-(2-methoxyethyl)-3-p-trifluoromethylbenzoyl-4-phenyl-4-imidazolin-2-one | φH—ETOH (3:1) | 60° | 1000 | 4 | 1.7:1.0 | 26% |
| 1-(2-methoxyethyl)-3-(1-adamantanecarbonyl)-4-phenyl-4-imidazolin-2-one | φH—ETOH (3:1) | 60° | 1000 | 4 | 1.2:1.0 | 9.1% |
| 1-(2-methoxyethyl)-3-o-anisoyl-4-phenyl-4-imidazolin-2-one | φH—ETOH (3:1) | 60° | 1000 | 4 | 1.5:1.0 | 20.0% |
| 1-(2-methoxyethyl)-3-acetyl-4-phenyl-4-imidazolin-2-one | φH—Pr'OH (3:1) | 60° | 500 | 6 | 2.0:1.0 | 33% | a pale yellow solid; m.p. 114°–117° C.

EXAMPLE 19

Preparation of other 1-(2-methoxyethyl)-3-acyl-4-phenyl-4-imidazolin-2-ones

The following acyl derivatives are prepared by procedures identical to that described for the N-benzoyl derivative of Example 18:

(a) 1-(2-methoxyethyl)-3-cyclohexanecarbonyl-4-phenyl-4-imidazolin-2-one;
(b) 1-(2-methoxyethyl)-3-p-trifluoromethylbenzoyl-4-phenyl-4-imidazolin-2-one;
(c) 1-(2-methoxyethyl)-3-(1-adamantanecarbonyl)-4-phenyl-4-imidazolin-2-one;
1-(2-methoxyethyl)-3-o-anisoyl-4-phenyl-4-imidazolin-2-one;
(e) 1-(2-methoxyethyl)-3-(2-chlorobenzoyl)-4-phenyl-4-imidazolin-2-one;
(f) 1-(2-methoxyethyl)-3-(2,4-dichlorobenzoyl)-4-phenyl-4-imidazolin-2-one; and
(g) 1-(2-methoxyethyl)-3-(2-methylbenzoyl)-4-phenyl-4-imidazolin-2-one.

EXAMPLE 20

Hydrogenation of N-acyl derivatives of 1-(2-methoxyethyl)-4-phenyl-4-imidazolin-2-one using (+)DIOP RhCODCl Catalyst and Hydrogen The hydrogenations are carried out in a Parr Shaker apparatus or in a high pressure laboratory in glass lined autoclaves. The products are extracted with ether or ether-benzene, concentrated and hydrolyzed by refluxing in a 10 percent sodium hydroxide solution. The crude 1-(2-methoxyethyl)-4-phenyl-2-imidazolidone generated is extracted with methylene chloride, concentrated, and analyzed for the ratio of enantiomers by Nuclear Magnetic Resonance (NMR) using the chiral shift reagent tris-[-3-(trifluoromethylhydroxymethylene)-d-camphorato], europium (III) derivative,

EXAMPLE 21

Optically Active Levamisole from 1-(2-methoxyethyl)-4-phenyl-3-acetyl-4-imidazolin-2-one Approximately 5.2 g. of 1-(2-methoxyethyl)-4-acetyl-4-phenyl-4-imidazolin-2-one, 250 mg. of cyclooctadiene rhodium chloride dimer and 600 mg. of (+)DIOP dissolved under nitrogen in 30 ml. of ethanol and 30 ml of benzene is hydrogenated in a Parr Shaker apparatus at 40° C. and 35 psig hydrogen for 11 hours. The solution is concentrated to dryness under reduced pressure, the residue dissolved in ether (100 ml.) and filtered. The filtrate is concentrated under reduced pressure to give a brown oil. This oil is dissolved in 20 ml of ethanol and 40 ml. of 10 percent sodium hydroxide is added. The mixture is refluxed for 1 hour, cooled and extracted with methylenechloride (2.′.50 ml.) The combined organic layer is washed, dried and the solvent removed to give optically active 1-(2-methoxyethyl)-4-phenyl-2-imidazolidone as a waxy solid. This material is estimated to contain 24 percent excess of one enantiomer using the chiral shift reagent Eu(tfc)₃ mentioned in Example 20. The solid is refluxed with 2 g of phosphorous pentasulfide in toluene for 20 hours. Toluene is removed under reduced pressure, the residue taken up in 100 ml of chloroform and 100 ml. of 20 percent sodium hydroxide. The organic layer is separated, washed and concentrated to give an oil. This oil is taken in 20 ml of concentrated hydrochloric acid and the solution is refluxed for 1 hour. The solution is cooled, filtered and filtrate made basic with ammonium hydroxide. The mixture is extracted with 2×50 ml of methylene chloride. The combined organic layer is washed, dried and the solvent removed to give an oil which crystallizes on standing. The spectral characteristics are identical to that of tetramisole and the material had a specific rotation $[\alpha]_D^{20} = -17.7°$ (c7 in chloroform) corresponding to a 21% enantiomeric excess of levamisole.

EXAMPLE 22

Optically Active Levamisole from 1-(2-methoxyethyl)-3-benzoyl-4-phenyl-4-imidazolin-2-one Approximately 6.4 g of 1-(2-methoxyethyl)-3-benzoyl-4-phenyl-4-imidazolin-2-one, 250 mg. of cyclooctadiene rhodium chloride dimer and 550 gm of (+)DIOP dissolved in 30 ml of ethanol and 30 ml of benzene is hydrogenated in a Parr Shaker apparatus at 40° C. and 45 psig of hydrogen for 18 hours. The solution is then concentrated under reduced pressure and the residue extracted with ether (3×75 ml.). The ether extracts are combined and concentrated to give 6.3 g of an oil. This oil is hydrolyzed by refluxing with 10 percent sodium hydroxide solution and optically active 1-(2-methoxyethyl)-4-phenyl-2-imidazolidone is obtained as described in Example 21. The material is estimated to contain a 26 percent excess of one enantiomer. Further conversion of this material to levamisole as described in Example 21 gives optically active levamisole with a specific rotation $[\alpha]_D^{CO} -17.9$ (C 10, chloroform), corresponding to a 22 percent excess of levamisole.

EXAMPLE 23

1-(2-butoxyethyl)-4-phenyl-4-imidazolin-2-one

Phenacyl bromide (10 g) in 50 ml of chloroform is added over 20 minutes to a mixture of 2-butoxyethylamine (6 g) and triethylamine (7 g) in 50 ml of chloroform at 0° C. The mixture is stirred for 2 hours. Water (100 ml) is added, the organic layer separated, cooled to 0° C. and glacial acetic acid (5 ml), potassium cyanate (5 g) and methanol (20 ml) are added. The mixture is refluxed for ninety minutes, cooled, washed with saturated sodium bicarbonate solution, dried, and solvent removed to give the title product.

EXAMPLE 24

1-(2-butoxyethyl)-4-phenyl-2-inidazolidone

A solution of 1-(2-butoxyethyl)-4-phenyl-4-imidazolin-2-one in ethanol with 10% palladium or carbon catalyst is reduced in an atmosphere of hydrogen. After the theoretical amount of hydrogen is absorbed, the catalyst is filtered and filtrate concentrated to give the title compound.

EXAMPLE 25

1-(2-methoxyethyl)-4-(2-chlorophenyl)-4-imidazolin-2-one

To o-chlorophenacyl bromide (23.4 g) in 100 ml of chloroform is added over 30 minutes 2-methoxyethylamine (20 g). in 100 ml of chloroform which is cooled with an ice bath. The mixture is stirred for an additional hour at 0° C. Water (200 ml) is added and the organic layer is separated, cooled to 0° C. with an ice bath and then glacial acetic acid (8 ml), potassium cyanate 0 g) and methanol are added. The mixture is refluxed for 90 minutes, cooled, washed with saturated sodium bicarbonate solution, dried over anhydrous sodium sulfate and solvent removed to give the title product.

EXAMPLE 26

1-(2-methoxyethyl)-4-(substituted phenyl)-4-imidazolin-2-ones

The following 1-(2-methoxyethyl)-4-(substituted phenyl)-4-imidazolin-2-ones are prepared in an identical manner to that described in Example 25:
(a) 1-(2-methoxyethyl)-4-(2,4-dichlorophenyl)-4-imidazolin-2-one and
(b) 1-(2-methoxyethyl)-4-(p-trifluoromethylphenyl)-4-imidazolin-2-one.

EXAMPLE 27

Preparation of 1-(2-methoxyethyl)-4-(substituted phenyl)-2-imidazolidone

A solution of 1-(2-methoxyethyl)-4-(substituted phenyl)-4-imidazolin-2-one in ethanol with 10% palladium or carbon catalyst is reduced at from about 15 psig hydrogen to about 1000 psig hydrogen. After the theoretical amount of hydrogen is absorbed, the catalyst is filtered and the filtrate is concentrated to give the 1-(2-methoxyethyl)-4-(substituted phenyl)-2-imidazolidones. The following compounds were prepared in the above manner:
(a) 1-(2-methoxyethyl)-4-(m-trifluoromethyl)-2-imidazolidone;
(b) 1-(2-methoxyethyl)-4-(m-methyl phenyl)-2-imidazolidone;
(c) 1-(2-methoxyethyl)-4-(p-trifluoromethylphenyl)-2-imidazolidone; and
(d) 1-(2-methoxyethyl)-4-(m-methoxyphenyl)-2-imidazolidone.

EXAMPLE 28

1-(2-benzoyloxyethyl)-4-phenyl-4-imidazolin-2-one

Approximately 15 g of 2-phenyloxazoline and 20 g of phenacy bromide is refluxed in 100 ml of chloroform for 1 hour. The solvent is concentrated under reduced pressure and acetic acid (10 ml), potassium cyanate (9 g) and methanol (100 ml) are added and the mixture refluxed for 1 hour. The mathanol is removed under reduced pressure and the residue taken up in 200 ml of methylene chloride and washed with saturated sodium bicarbonate solution. The organic layer is dried and concentrated to give the title compound.

EXAMPLE 29

Preparation of other 1-(2-acyloxyethyl)-4-phenyl-4-imidazolin-2-ones

The following 1-(2-acyloxyethyl)-4-phenyl-4-imidazollin-2-ones are prepared by procedures identical to that described for the benzoyloxy derivatives of Example 28:
(a) 1-[2-(propionyloxy)ethyl]-4-phenyl-4-imidazolin-2-ones;
(b) 1-2-(p-methylbenzoyloxy)ethyl-1-[2-(p-nitrobenzoyloxy)ethyl]-4-phenyl-4-kmidazolin-2-one; and
(c) 1-[2-(p-trifluoromethylbenzoyloxy)ethyl]-4-phenyl-4-imidazolin.

EXAMPLE 30

Preparation of 1-(2-acyloxyethyl)-4-phenyl-2-imidazolidones

The following 1-(2-acyloxyethyl)-4-phenyl-2-imidazolidones are prepared by the catalytic reduction of 1-(2-acyloxyethyl)-4-phenyl-4-imidazolin-2-ones identical to that described for 1-(2-acetoxyethyl) derivatives of Example 13:
(a) 1-[2-benzoyloxyethyl]-4-phenyl-2-imidazolidone;
(b) 1-[2-propionyloxy)ethyl]-4-phenyl-2-imidazolidone;
(c) 1-[2-(pmethylbenzoyloxy)ethyl]-4-phenyl-2-imidazoline; and
(d) 1-[2-(p-trifluoromethylbenzoyloxy)ethyl)ethyl]-4-phenyl-2-imidazolidone.

EXAMPLE 31

The following amino ketones of Formula A are prepared by the reaction of the corresponding derivatized ethanolamines of their acid addition salts with the corresponding phenacyl bromides as in the first three sentences of Example 2:

$$R_2CCH_2NHCH_2CH_2 \text{ or}$$
(A)

| $R_2$ | R |
|---|---|
| $C_6H_5$ | $C_2H_5$ |
| $C_6H_5$ | $C_3H_7$—i |
| $C_6H_5$ | $CH_2CH_2Cl$ |
| $C_6H_5$ | $C_6H_5$ |
| $C_6H_5$ | $C_6H_4$—(p-$CH_3$) |
| $C_6H_5$ | $C_6H_4$—(p-Cl) |
| $C_6H_5$ | $C_6H_4$—(p-$OCH_3$) |
| $C_6H_5$ | $C_6H_4$—(m-$OCH_3$) |
| $C_6H_5$ | $C(O)C_2H_5$ |
| $C_6H_5$ | $C(O)C_4H_9$ |
| $C_6H_5$ | $C(O)OCH_3$ |
| $C_6H_5$ | $C(O)OC_6H_5$ |
| m-$OCH_3$—$C_6H_4$ | $CH_3$ |
| m-CL—$C_6H_4$ | H |
| m-Br—$C_6H_4$ | H |
| m-Cl—$C_6H_4$ | $C(O)CH_3$ |
| $C_6H_5$ | $C(O)OC_6H_4$(p-$CH_3$) |
| $C_6H_5$ | $C(O)OC_6H_4$(o-$CH_3$) |
| $C_6H_5$ | $C(O)OC_6H_4$(P—$OCH_3$) |
| $C_6H_5$ | $C(O)C_6H_5$ |
| $C_6H_5$ | $C(O)C_6H_4$(p-$CH_3$) |
| $C_6H_5$ | $C(O)C_6H_4$(p-$OCH_3$) |
| $C_6H_5$ | $C(O)C_6H_4$(m-$CF_3$) |
| m-Br—$C_6H_4$ | $C(O)C_6H_5$ |
| m-$CF_3$—$C_6H_4$ | $CH_3$ |
| m-$CH_3$—$C_6H_4$ | $CH_3$ |
| m-Cl—$C_6H_4$ | $C_6H_5$ |
| M—$CF_3$—$C_6H_4$ | $C(O)OCH_3$ |
| P—Cl—$C_6H_4$ | $CH_3$ |
| m-Br—$C_6H_4$ | $C_2H_5$ |

The substituted ethanolamine and their acid addition salts and phenacyl bromide starting materials are proposed by known literature methods.

EXAMPLE 32

The following imidazolinones of Formula B are prepared from aminoketones prepared as in Example 30 by the reaction with potassium cyanate as in Examples 1 and 2:

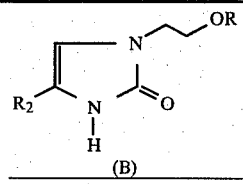
(B)

| $R_2$ | R |
|---|---|
| $C_6H_5$ | $C_2H_5$ |
| $C_6H_5$ | $C_3H_7$—i |
| $C_6H_5$ | $CH_2CH_2Cl$ |
| $C_6H_5$ | $C_6H_5$ |
| $C_6H_5$ | $C_6H_4$(p-$CH_3$) |
| $C_6H_5$ | $C_6H_4$(p-Cl) |
| $C_6H_5$ | $C_6H_4$(p-$OCH_3$) |
| $C_6H_5$ | $C_6H_4$(m-$OCH_3$) |
| $C_6H_5$ | $C(O)C_2H_5$ |
| $C_6H_5$ | $C(O)C_4H_9$ |
| $C_6H_5$ | $C(O)OCH_3$ |
| $C_6H_5$ | $C(O)OC_6H_5$ |
| $C_6H_5$ | $C(O)OC_6H_4$(p-$CH_3$) |
| $C_6H_5$ | $C(O)OC_6H_4$(o-$CH_3$) |
| $C_6H_5$ | $C(O)OC_6H_4$(p-$OCH_3$) |
| $C_6H_5$ | $C(O)C_6H_5$ |
| $C_6H_5$ | $C(O)C_6H_4$(p-$CH_3$) |
| $C_6H_5$ | $C(O)C_6H_4$(p-$OCH_3$) |
| $C_6H_5$ | $C(O)C_6H_4$(m-$CF_3$) |
| m-Br—$C_6H_4$ | $C(O)C_6H_5$ |
| m-$CF_3$—$C_6H_4$ | $CH_3$ |
| m-$CH_3$—$C_6H_4$ | $CH_3$ |
| m-$OCH_3$—$C_6H_4$ | $CH_3$ |
| m-Cl—$C_6H_4$ | H |
| m-Br—$C_6H_4$ | H |
| m-Cl—$C_6H_4$ | $C(O)CH_3$ |
| m-Cl—$C_6H_4$ | $C_6H_5$ |
| m-$CF_3$—$C_6H_4$ | $C(O)OCH_3$ |
| p-Cl—$C_6H_4$ | $CH_3$ |
| m-Br—$C_6H_4$ | $C_2H_5$ |

EXAMPLE 33

The following 3-substituted imidazolinones of Formula C are prepared as in Example 18 using the appropriate carbonyl holides or anhydrides and the corresponding 3-H-imidazolinones:

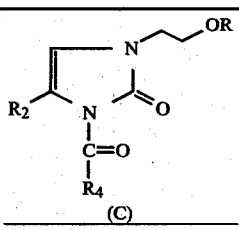
(C)

| $R_2$ | R | $R_4$ |
|---|---|---|
| $C_6H_5$ | $C_2H_5$ | $CH_3$ |
| $C_6H_5$ | $C_3H_7$—i | $C_6H_5$ |
| $C_6H_5$ | $CH_2CH_2Cl$ | $CH_3O$ |
| $C_6H_5$ | $C_6H_5$ | $C_6H_5O$ |
| $C_6H_5$ | $C_6H_4$(p-$CH_3$) | $CH_3$ |
| $C_6H_5$ | $C_6H_4$(p-Cl) | cyclobutyl |
| $C_6H_5$ | $C_6H_4$(p-$OCH_3$) | $C_6H_5$ |
| $C_6H_5$ | $C_6H_4$(m-$OCH_3$) | $C_2H_5$ |
| $C_6H_5$ | $C(O)C_2H_5$ | $CH_3$ |
| $C_6H_5$ | $C(O)C_4H_9$ | $C_6H_4$(p-$CH_3$) |
| $C_6H_5$ | $C(O)OCH_3$ | $CH_3$ |
| $C_6H_5$ | $C(O)OC_6H_5$ | $C_2H_5$ |
| $C_6H_5$ | $C(O)OC_6H_4$(p-$CH_3$) | $C_6H_3$(2,4-di-$CH_3$) |
| $C_6H_5$ | $C(O)OC_6H_4$(o-$OCH_3$) | $CH_3$ |
| $C_6H_5$ | $C(O)OC_6H_4$(p-$OCH_3$) | $C_3H_7$ |
| $C_6H_5$ | $C(O)C_6H_5$ | $C_2H_5O$ |
| $C_6H_5$ | $C(O)C_6H_4$(p-$CH_3$) | cyclohexyl |
| $C_6H_5$ | $C(O)C_6H_4$(p-$OCH_3$) | $C_6H_4$(p-$CF_3$) |

-continued

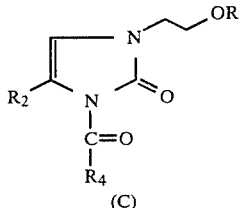

| $R_2$ | R | $R_4$ |
|---|---|---|
| $C_6H_5$ | $C(O)C_6H_4(m-CF_3)$ | $C_6H_4O(p-CH_3)$ |
| m-Br—$C_6H_4$ | $C(O)C_6H_5$ | $C_4H_9O$ |
| m-$CF_3$—$C_6H_4$ | $CH_3$ | $C_6H_4(p-OCH_3)$ |
| m-$CH_3$—$C_6H_4$ | $CH_3$ | $CH_3$ |
| m-$CH_3O$—$C_6H_4$ | $CH_3$ | i-$C_3H_7$ |
| m-Cl—$C_6H_4$ | H | $C_6H_5$ |
| m-Br—$C_6H_4$ | H | $C_6H_4(m-Cl)$ |
| m-Cl—$C_6H_4$ | $C(O)CH_3$ | $C_6H_4(p-CH_3O)$ |
| m-Cl—$C_6H_4$ | $C_6H_5$ | $C_6H_4(p-CH_3)O$ |
| m-$CF_3$—$C_6H_4$ | $C(O)OCH_3$ | $CH_3$ |
| p-Cl—$C_6H_4$ | $CH_3$ | $C_4H_9OC(O)$ |
| m-Br—$C_6H_4$ | $C_2H_6$ | $C_6H_5$ |

EXAMPLE 34

The following 3-substituted imidazolidones of Formula D are prepared by catalytic hydrogenation of the corresponding 3-substituted imidazolinony using the procedure of Example 13:

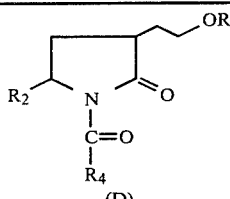

| $R_2$ | R | $R_4$ |
|---|---|---|
| $C_6H_5$ | $C_2H_5$ | $CH_3$ |
| $C_6H_5$ | $C_3H_7$—i | $C_6H_5$ |
| $C_6H_5$ | $C_2H_5$ | $CH_3O$ |
| $C_6H_5$ | $C_6H_5$ | $C_6H_5O$ |
| $C_6H_5$ | $C_6H_4(p-CH_3)$ | $CH_3$ |
| $C_6H_5$ | $C_6H_5$ |  |
| $C_6H_5$ | $C_6H_4(p-OCH_3)$ | $C_6H_5$ |
| $C_6H_5$ | $C_6H_4(m-OCH_3)$ | $C_2H_5$ |
| $C_6H_5$ | $C(O)C_2H_5$ | $CH_3$ |
| $C_6H_5$ | $C(O)C_4H_9$ | $C_6H_4(p-CH_3)$ |
| $C_6H_5$ | $C(O)OCH_3$ | $CH_3$ |
| $C_6H_5$ | $C(O)C_6H_5$ | $C_2H_5$ |
| $C_6H_5$ | $C(O)OC_6H_4(p-CH_3)$ | $C_6H_3(2,4$-di-$CH_3)$ |
| $C_6H_5$ | $C(O)OC_6H_4(o-CH_3)$ | $CH_3$ |
| $C_6H_5$ | $C(O)OC_6H_4(p-OCH_3)$ | $C_3H_7$ |
| $C_6H_5$ | $C(O)C_6H_5$ | $C_2H_5O$ |
| $C_6H_5$ | $C(O)C_6H_4(p-CH_3)$ |  |
| $C_6H_5$ | $C(O)C_6H_4(p-OCH_3)$ | $C_6H_4(p-CF_3)$ |
| $C_6H_5$ | $C(O)C_6H_4(m-CF_3)$ | $C_6H_4O(p-CH_3)$ |
| m-$CF_3C_6H_4$ | $CH_3$ | $C_6H_4(p-OCH_3)$ |
| m-$CH_3C_6H_4$ | $CH_3$ | $CH_3$ |
| m-$CH_3O$—$C_6H_4$ | $CH_3$ | i-$C_3H_7$ |
| m-$CF_3$—$C_6H_4$ | $C(O)OCH_3$ | $CH_3$ |

If the corresponding Formula C compounds are hydrogenated in the presence of a homogeneous hydrogenation catalyst such as tristriphenylphosphino chlororhodium, the following compounds of Formula D are prepared:

| $R_2$ | R | $R_4$ |
|---|---|---|
| m-Br-$C_6H_4$ | $C(O)C_6H_5$ | $C_4H_9O$ |
| m-Cl-$C_6H_4$ | H | $C_6H_5$ |
| m-Br-$C_6H_4$ | H | $C_6H_4(m-Cl)$ |
| m-Cl-$C_6H_4$ | $C(O)CH_3$ | $C_6H_4(p-CH_3O)$ |
| m-Cl-$C_6H_4$ | $C_6H_5$ | $C_6H_4(p-CH_3)O$ |
| p-Cl-$C_6H_4$ | $CH_3$ | $C_4H_9OC(O)$ |
| m-Br-$C_6H_4$ | $C_2H_4$ | $C_6H_5$ |

EXAMPLE 35

The following imidazolidones of Formula E are prepared by hydrogenation of the corresponding 3-unsubstituted imidazolinones according to the procedure of Example 3:

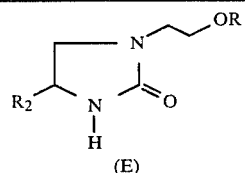

| $R_2$ | R |
|---|---|
| $C_6H_5$ | $C_2H_5$ |
| $C_6H_5$ | $C_3H_7$—i |
| $C_6H_5$ | $C_6H_5$ |
| $C_6H_5$ | $C_6H_4(p-CH_3$ |
| $C_6H_5$ | $C_6H_4(p-OCH_3)$ |
| $C_6H_5$ | $C_6H_4(m-OCH_3)$ |
| $C_6H_5$ | $C(O)C_2H_5$ |
| $C_6H_5$ | $C(O)C_4H_9$ |
| $C_6H_5$ | $C(O)OCH_3$ |
| $C_6H_5$ | $C(O)OC_6H_5$ |
| $C_6H_5$ | $C(O)OC_6H_4(p-CH_3)$ |
| $C_6H_5$ | $C(O)OC_6H_4(o-CH_3)$ |
| $C_6H_5$ | $C(O)C_6H_5$ |
| $C_6H_5$ | $C(O)C_6H_4(p-CH_3)$ |
| $C_6H_5$ | $C(O)C_6H_4(p-OCH_3)$ |
| $C_6H_5$ | $C(O)C_6H_4(m-CF_3)$ |
| m-$CF_3$—$C_6H_4$ | $CH_3$ |
| m-$CH_3$—$C_6H_4$ | $CH_3$ |
| m-$OCH_3$—$C_6H_4$ | $CH_3$ |
| m-$CF_3$—$C_6H_4$ | $C(O)OCH_3$ |

All of the above compounds and the following compounds can be prepared by hydrolysis of the corresponding formula D compounds of Example 34.

| $R_2$ | R |
|---|---|
| $C_6H_5$ | $C_6H_4(p-Cl)$ |
| $C_6H_5$ | $CH_2CH_2Cl$ |
| m-Br—$C_6H_4$ | $C(O)C_6H_5$ |
| m-Cl—$C_6H_4$ | H |
| m-Br—$C_6H_4$ | H |
| m-Cl—$C_6H_4$ | $C(O)CH_3$ |
| m-Cl—$C_6H_4$ | $C_6H_5$ |
| p-Cl—$C_6H_4$ | $CH_3$ |
| m-Br—$C_6H_4$ | $C_2H_5$ |

EXAMPLE 36

The following imidazolidine-2-thiones of Formula F are prepared as in Example 4 from the corresponding 3-unsubstituted imidazolidones as in Example 4:

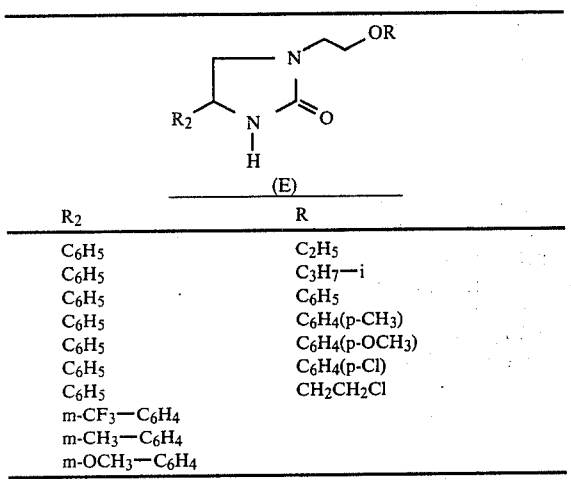

| $R_2$ | R |
|---|---|
| $C_6H_5$ | $C_2H_5$ |
| $C_6H_5$ | $C_3H_7$—i |
| $C_6H_5$ | $C_6H_5$ |
| $C_6H_5$ | $C_6H_4(p\text{-}CH_3)$ |
| $C_6H_5$ | $C_6H_4(p\text{-}OCH_3)$ |
| $C_6H_5$ | $C_6H_4(p\text{-}Cl)$ |
| $C_6H_5$ | $CH_2CH_2Cl$ |
| m-$CF_3$—$C_6H_4$ | |
| m-$CH_3$—$C_6H_4$ | |
| m-$OCH_3$—$C_6H_4$ | |

We claim:

1. A method for the preparation of an optically active compound of the formula:

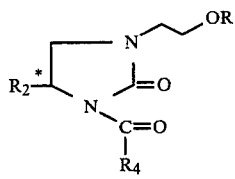

wherein R is selected from the group consisting of hydrogen, $C_1$-$C_6$ alkyl, halo $C_1$-$C_6$ alkyl, phenyl, phenyl substituted with up to three groups selected from the group consisting of $C_1$-$C_6$ alkyl, halo and $C_1$-$C_6$ alkoxy and a moiety of the formula $COR_3$, wherein $R_3$ is selected from the group consisting of hydrogen, $C_1$-$C_6$ alkyl $C_1$-$C_6$ alkoxy, phenoxy, halo $C_1$-$C_6$ alkyl, phenyl, and phenyl or phenoxy substituted with up to four groups selected from the group consisting of $C_1$-$C_6$ alkyl, halo, trifluoromethyl and $C_1$-$C_6$ alkoxy; $R_4$ is selected from the group consisting of $C_1$-$C_6$ alkyl $C_1$-$C_6$ alkoxy, phenoxy, $C_5$-$C_{10}$ cycloalkyl, phenyl, and phenyl or phenoxy substituted with up to four groups selected from the group consisting of $C_1$-$C_6$ alkyl, halo, trifluoromethyl and $C_1$-$C_6$ alkoxy; and $R_2$ is selected from the group consisting of phenyl and phenyl substituted with up to two groups selected from the group consisting of $C_1$-$C_6$ alkyl, $C_1$-$C_6$ alkoxy, halo and trifluoromethyl which comprises reducing an imidazolinone of formula:

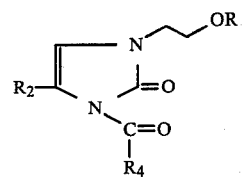

wherein R, $R_4$ and $R_3$ are as previously defined, by hydrogenating in the presence of a chiral catalyst in a suitable organic solvent at a temperature from about 25° to 80° C. to obtain an optically active imidazolidone of formula:

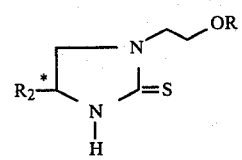

wherein R, $R_4$ and $R_2$ are as previously defined.

2. The method according to claim 1, wherein said suitable organic solvent is selected from the group consisting of alcohol, aromatic hydrocarbons, ketones and ethyl acid esters.

3. The method according to claim 1, wherein said chiral catalyst is (+)2,3-isopropylidene-2,3-dihydroxy-1,4-bis(diphenylphosphino)butane Rh CODCl.

4. A method for the preparation of an optically active compound of the formula:

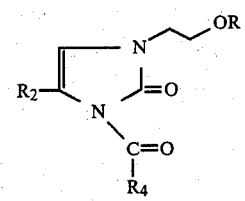

wherein R is selected from the group consisting of $C_1$-$C_6$ alkyl, halo $C_1$-$C_6$ alkyl, phenyl, phenyl substituted with up to three groups selected from the group consisting of $C_1$-$C_6$ alkyl, halo and $C_1$-$C_6$ alkoxy to alkyl, and $R_2$ is selected from the group consisting of phenyl and phenyl substituted with up to two groups selected from the group consisting of $C_1$-$C_6$ alkyl, $C_1$-$C_6$ alkoxy, halo and trifluoromethyl; which comprises reducing an imidazolinone of formula:

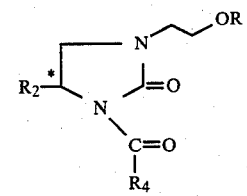

wherein R, and $R_2$ are as previously defined and $R_4$ is selected from the group consisting of $C_1$-$C_6$ alkyl $C_1$-$C_6$ alkoxy, phenoxy, $C_5$-$C_{10}$ cycloalkyl, phenyl, and phenyl or phenoxy substituted with up to four groups selected from the group consisting of $C_1$-$C_6$ alkyl, halo trifluoromethyl and $C_1$-$C_6$ alkoxy; by hydrogenating in the presence of a chiral catalyst in a suitable solvent such as ester alcohol or aromatic solvent at a temperature from about 25° to 80° C. to obtain an optically active imidazolidone of formula:

wherein R, $R_2$ and $R_4$ are as previously defined, hydrolyzing off the $COR_4$ substituent in the presence of a hydroxide source in either water or alcohol at a temperature from about 70° to 100° C. to obtain an optically active imidazolidone of the formula:

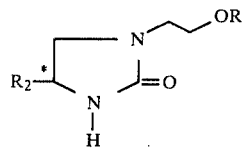

wherein R and R₂ are as previously defined, refluxing said optically active imidazolidone with a reagent capable of substituting sulfur for oxygen in a suitable solvent at a temperature from about 80° to 200° C.

5. The method according to claim 3, wherein said chiral catalyst is (+)2,3-isopropylidene-2,3-dihydroxy-1,4-bis(diphenylphosphino)butane Rh CODCl.

* * * * *